(12) United States Patent
Griffith

(10) Patent No.: US 6,585,744 B1
(45) Date of Patent: Jul. 1, 2003

(54) SURGICAL SEWING DEVICE

(75) Inventor: John Dalton Griffith, Sunderland (GB)

(73) Assignee: Griffith Textile Machines, Ltd., Tyne & Wear (GB)

( * ) Notice: Subject to any disclaimer, the term of this patent is extended or adjusted under 35 U.S.C. 154(b) by 0 days.

(21) Appl. No.: 09/763,035

(22) PCT Filed: Aug. 12, 1999

(86) PCT No.: PCT/GB99/02651
§ 371 (c)(1),
(2), (4) Date: Feb. 15, 2001

(87) PCT Pub. No.: WO00/10467
PCT Pub. Date: Mar. 2, 2000

(30) Foreign Application Priority Data

Aug. 19, 1998 (GB) .............................. 9817995

(51) Int. Cl.⁷ .............................................. A61B 17/04
(52) U.S. Cl. ..................................................... 606/144
(58) Field of Search ................................ 606/144, 146; 112/169

(56) References Cited

U.S. PATENT DOCUMENTS

| | | | | | |
|---|---|---|---|---|---|
| 3,435,789 | A | * | 4/1969 | Kuramochi | 112/169 |
| 4,484,580 | A | * | 11/1984 | Nomoto et al. | 606/146 |
| 4,841,888 | A | * | 6/1989 | Mills et al. | 112/169 |
| 6,221,085 | B1 | * | 4/2001 | Djurovic | 606/144 |

* cited by examiner

*Primary Examiner*—Ismael Izaguirre
(74) *Attorney, Agent, or Firm*—Nikolai & Mersereau, P.A.

(57) ABSTRACT

A sewing device comprising an elongate rigid support body having sewing means mounted at one end adapted to create a continuous chain stitch and drive means located at the opposite end operable for driving the sewing means.

40 Claims, 5 Drawing Sheets

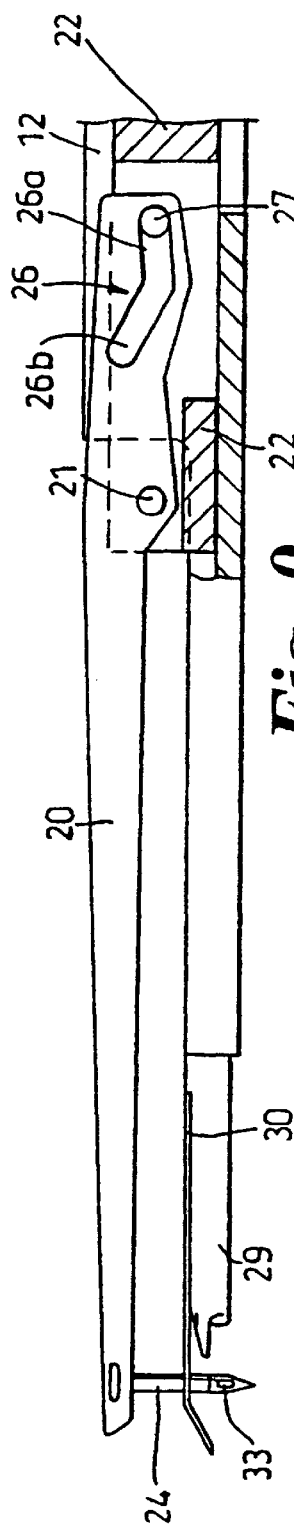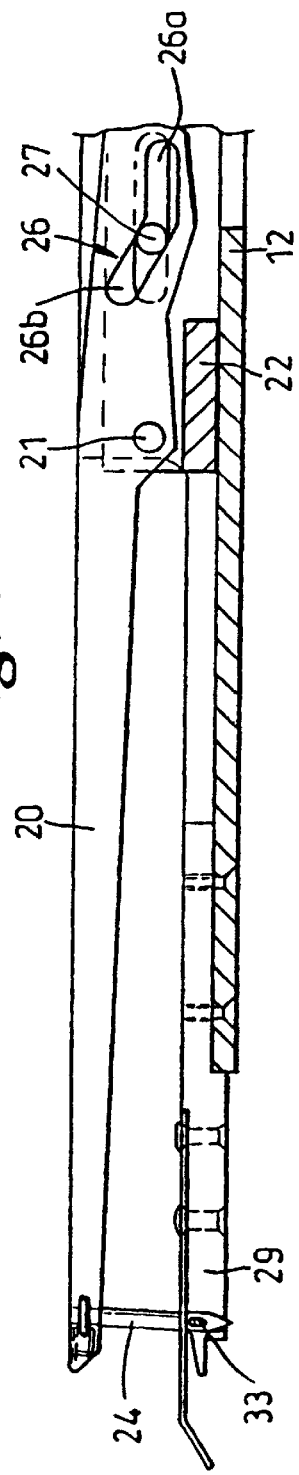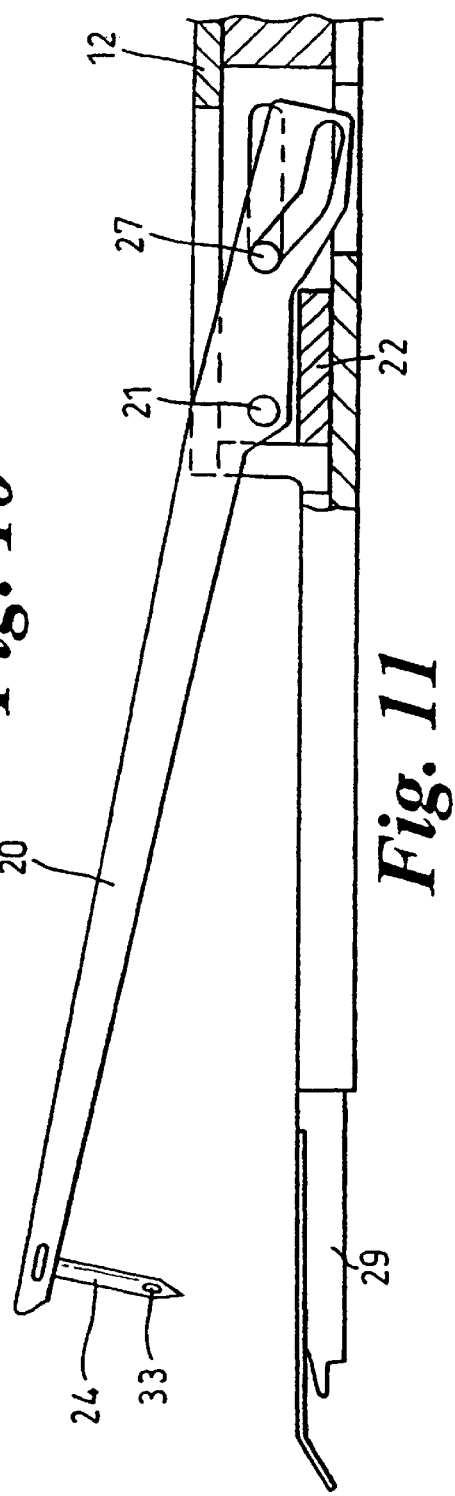

SURGICAL SEWING DEVICE

The present invention relates to a sewing device, in particular but not exclusively, a surgical sewing device.

When suturing a cut or wound it is normal practice for a surgeon to use a needle to form separate discrete stitches. This is a time consuming operation and is also difficult to perform for example in keyhole surgery.

An aim of the present invention is to provide a sewing device which can be operated by a surgeon to suture cuts in tissue by producing stitches mechanically. Another aim of the invention is to provide such a device which is capable of being operated externally of a patient in order to suture cuts in tissue located internally of the patient via a small incision.

According to one aspect of the present invention there is provided a sewing device comprising an elongate rigid support body having sewing means mounted at one end adapted to create a continuous chain stitch and drive means located at the opposite end operable for driving the sewing means. Preferably the drive means is arranged to drive the sewing means through a single sewing cycle only in order to produce a single stitch.

According to another aspect of the invention there is provided a method of suturing a cut or wound comprising mechanically sewing tissue adjacent the cut or wound to form a suture comprising a continuous chain stitch. Preferably the method comprises repeatedly positioning the sewing means at a manually selected position along the cut or wound to be sutured and operating the drive means to form a stitch at said selected position.

Various aspects of the present invention are hereinafter described with reference to the accompanying drawings, in which:

FIGS. 9,10 and 11 are part longitudinal sectional views of the sewing end of the device shown in different operating positions;

Figure 1:
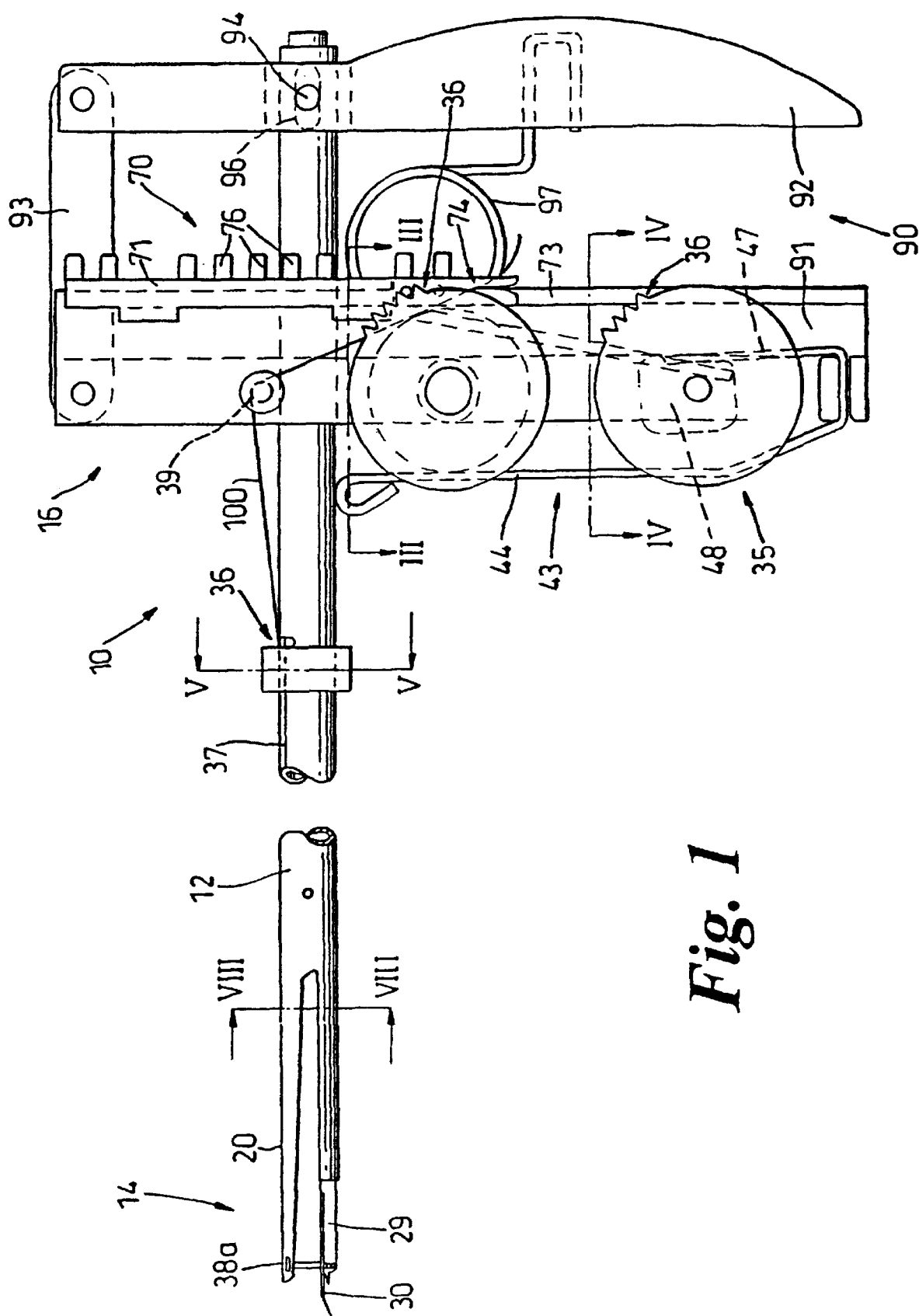
FIG. 1 is a side view of a sewing device according to an embodiment of the present invention.
Figure 2:
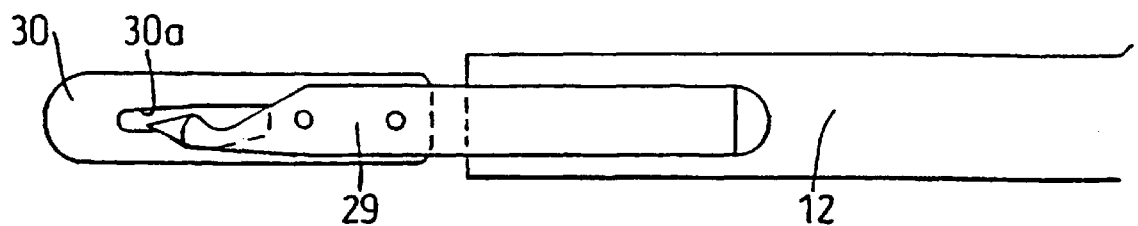
FIG. 2 is a plan view of the sewing end of the device shown in FIG. 1.
Figure 3:
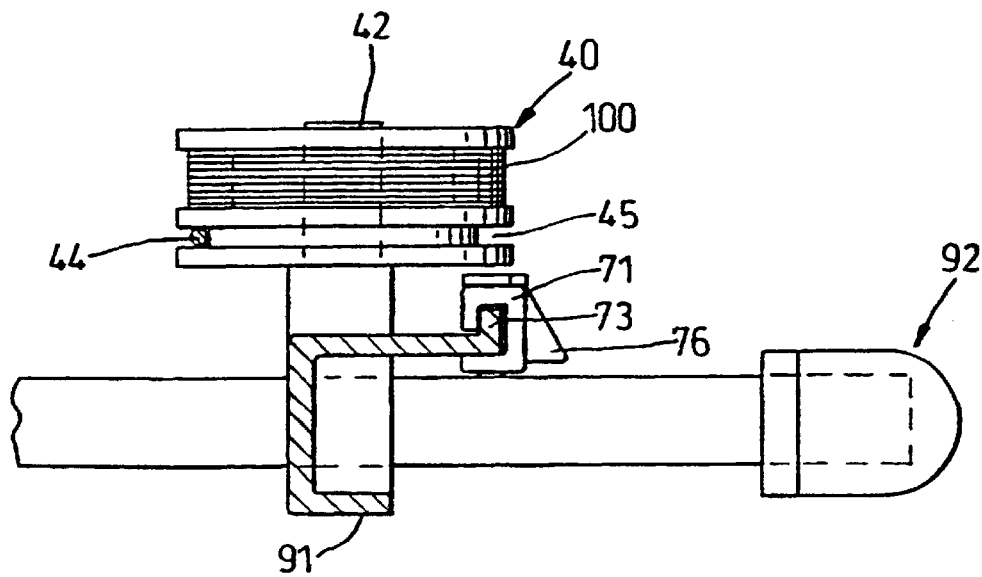
FIG. 3 is a sectional view taken along line III—III in FIG. 2.
Figure 4:
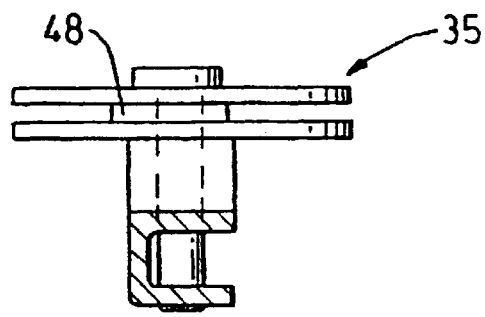
FIG. 4 is a sectional view taken along line IV—IV in FIG. 2.
Figure 5:
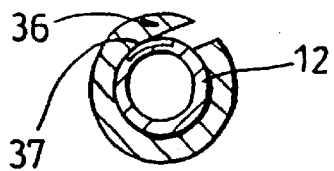
FIG. 5 is a sectional view taken along line V—V in FIG. 1.
Figure 6:
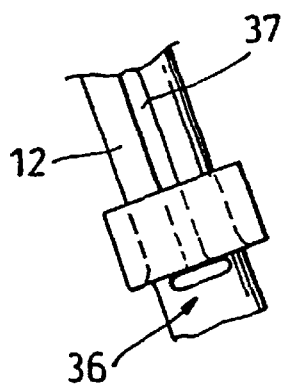
FIG. 6 is a part plan view of the device shown in FIG. 5.
Figure 8:
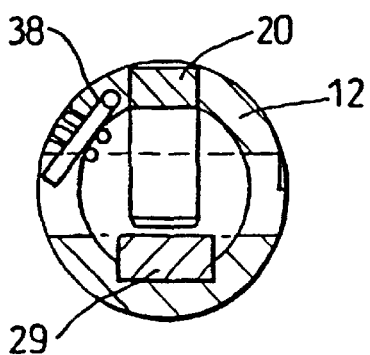
FIG. 8 is a sectional view taken along line VIII—VIII in FIG. 1.
Figure 7:
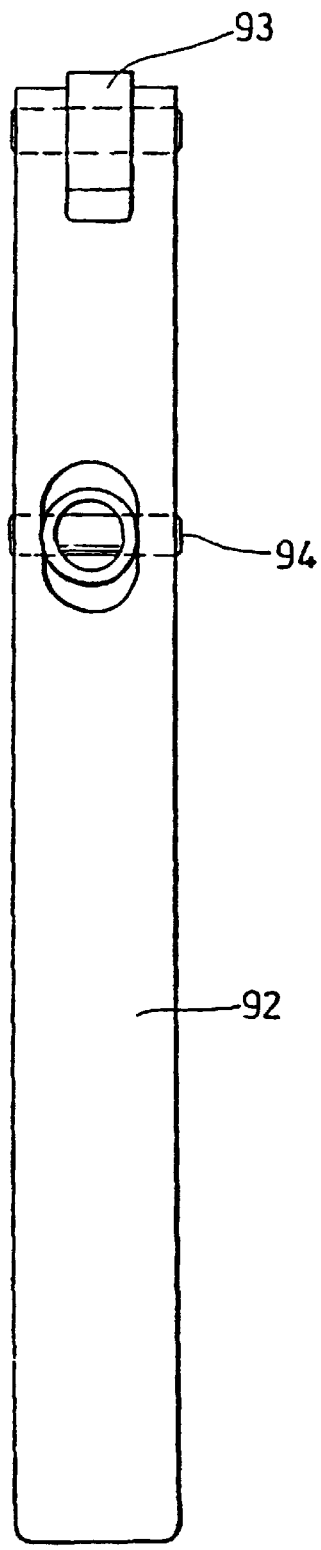
FIG. 7 is an end view of the device shown in FIG. 1.

Referring initially to FIG. 1 there is shown a sewing device 10 according to a preferred embodiment of the present invention.

The sewing device 10 includes a rigid support tube 12 which at one end supports a sewing means 14 and at the other end supports a manually operable drive means 16 for driving the sewing means 14.

The sewing means 14 includes a needle arm or lever 20 which is pivotally connected to a rigid push rod 22 by a pivot pin 21. A needle 24 is mounted on the terminal end of the lever 20. A looper arm 29 is fixedly mounted of the terminal end of the tube 12 for co-operation with the needle 24 for forming sewing stitches, viz. chain stitches.

Preferably a guide plate 30 is mounted between the lever 20 and looper arm 29 for shielding the looper 29 from snagging the material to be sewn during advancement of the device when producing a seam. The plate 30 includes an aperture 30a through which the needle 24 passes and through which stitch loops may also pass.

The push rod slidably extends through the hollow interior of the tube 12 to be connected to the drive means 16. Manual operation of the drive means causes the rod 22 to reciprocate within the tube 12.

The reciprocal motion of the push rod is converted to cause the needle lever 20 to pivot about the pin 21. This is preferably achieved by providing the lever 20 with a cranked slot 26 through which a guide pin 27 passes; the pin 27 being fixed to the rigid tube 12 such that reciprocation of the push rod 22 causes relative movement between the slot 26 and pin 27.

As seen in FIG. 9, when the rod 22 is located at its fully advanced position, the lever is located at a lowermost position relative to the looper arm 29. In this position the head of needle 24 carrying the thread eye 33 is located both beneath and in advance of the looper arm 29. In moving to this advanced position, the needle would have cleared the previously formed stitch from the looper arm 29.

FIG. 10 illustrates the rod 22 having moved partially back towards its fully retracted position. The pin 27 is shown to have left portion 26a of slot 26 and has begun to enter slot portion 26b. Slot portion 26a extends generally parallel to the axis of tube 12 and so whilst pin 27 is in this slot portion, the lever 20 remains at its lowermost position whilst the needle is moved along the longitudinal axis of the looper arm 29. This enables the looper arm during the retraction stroke of the rod 22 to pick up thread from the needle for forming the next stitch and also enables the needle during the advancement stroke of the rod 22 to clear the thread held on the looper arm 29.

FIG. 11 illustrates the rod 22 at its fully retracted position. In this position the lever 20 is located at an uppermost position relative to the looper arm 29. In this position, the pin 27 has entered and travelled to the terminal end of slot portion 26b and has thereby caused the lever to be moved to its raised position. In this position of the lever 20, the needle 24 is located both at a longitudinally retracted position and at an elevated spaced position relative to the looper arm 29. In this position, the needle 24 is clear of the material being sewn and so is able to advance for forming the next stitch.

Reciprocal movement of the rod 20 is controlled by the drive means 16.

The drive means 16 includes a handle 90 which is intended to be gripped in the hand of an operative.

The handle 90 comprises a first handle member 91 fixedly secured to the tube 12 and a second handle member 92 which is movably connected to the first handle member 91 by a pivotal linkage 93. The second handle member 92 is connected to the rod 20 by a drive pin 94 which passes through a slot 96 formed in the tube 12.

The first and second handle members are biased apart by a spring 97; this has the effect of biasing the rod 20 to its fully retracted position. Advancement of the rod 20 to its fully advanced position is achieved by the operative squeezing the first and second handle members toward one another. According the rate at which the rod is advanced and retracted is under the full control of the operative.

Thread 100 is stored on a bobbin 40 mounted on the first handle member 91. The bobbin 40 is rotatably located on a shaft 42 and has a tension control means 43 preferably in the form of a resilient arm 44 which frictionally engages within an annular groove 45 in order to control the rate of rotation of the bobbin 40 and so control the tension in the thread 100 being drawn from the bobbin.

Preferably the tension control means 43 is adapted so as to be capable of adjusting the tension applied by the bobbin. Preferably this is achieved by pivotally locating the lower end of arm 44 in the handle member 91 and providing a tension control arm 47 which resilienty engages with a cam 48. The cam 48 is provided on a wheel 35 rotatably mounted on the handle member 91. The wheel 35 is positioned so as to be capable of being contacted by the thumb on the hand of the operative. When rotated, wheel 35 via the cam 48 causes the arm 47 to move toward or away from the axis of wheel 35 and so decreases or increases the biasing force within arm 44.

Bobbin 40 is also located so as to be capable of being contacted by the thumb on the hand of the operative. Accordingly the operative is able to manually rotate the bobbin 40 in either direction in order to increase or decrease the tension applied by the tension control means 43. In this way the operative is able to positively control the tightness of the stitches and can vary the tightness from stitch to stitch.

Preferably the outer peripheries of both the bobbin 40 and wheel 35 are adapted, for example by the provision of appropriate knurling 36, to improve frictional contact with the thumb of the operative.

The thread 100 is guided from the bobbin 40 through a thread guide 36, along a groove 37 extending along the outer periphery of the tube 14, through a guide 38, through a guide 38a and to the eye 33 of the needle 24.

The thread 100 is then returned from the needle 24 through guide 38, groove 37 and guide 36 over a post 39 and is secured to stitch length control means 70 provided on the handle member 91. The length of thread returning from the needle to the control means 70 is referred hereinafter as the thread anchorage tail. The control means 70 acts to pull against the thread anchorage tail during the sewing process so as to advance the device along the seam being sewn.

Preferably the control means 70 comprises a slider 71 slidably located on a rail 73 formed on the handle member 91. A thread clamp 74 is provided on the slider 71 to secure the thread anchorage tail thereto. Friction means (not shown) are preferably provided for retaining the slider at desired locations along the rail 73.

The slider 71 is located at a position so that it can be contacted by the thumb of the operative. According during the sewing process, the operative can vary the stitch length on a stitch by stitch basis by moving the slider 71 by a desired amount. Preferably, the slider 71 is provided with projections 76 to facilitate grip by the thumb of the operative.

In use the device is threaded as shown in FIG. 1 with the slider 71 located in an uppermost position and with a thread anchorage tail secured thereto.

The sewing means 14 is then presented to the cut or wound to be sutured with the flesh to be sutured located between the raised needle 14 and looper arm 29.

Handle members 91,92 are the moved together and then allowed to return apart to form the first stitch. The slider 71 is then moved downwardly by a desired amount and this advances the device along the seam by pulling against the thread anchorage tail which is now secured to the flesh being sutured.

The handles 91,92 are now operated to produce the next stitch and the above steps are repeated to produce successive stitches along the seam. The sequence of stitch formation is illustrated in FIGS. 12 to 14.

Figure 12:
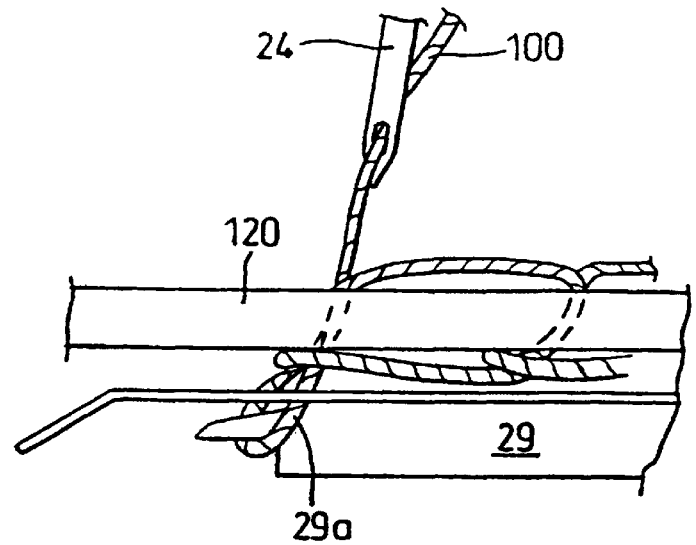
FIGS. 12, 13 and 14 illustrate successive stages in forming a sewing stitch using the device of FIG. 1.

In FIG. 12 the needle 24 is raised and is about to be advanced to the next stitch site. Advancement is achieved by moving slider 71. This has the effect of the looper arm 29 forming a loop 29a and in so doing draws thread 100 from the bobbin 40.

Figure 13:
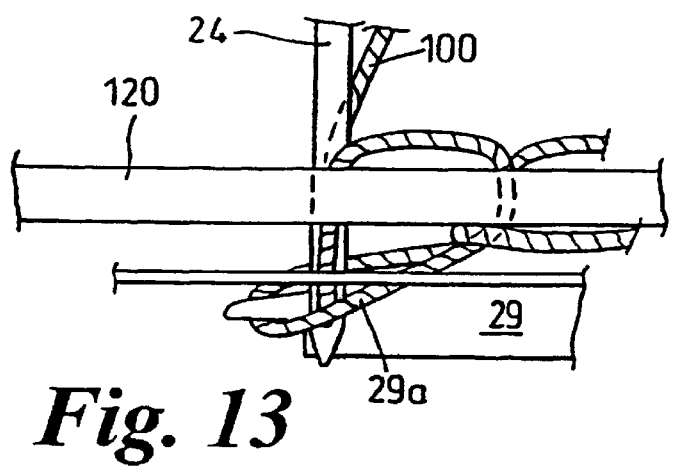

In FIG. 13, the needle 24 has advanced to the next needle site and when there, the handle members 91,92 have begun to be brought together. This causes the needle 24 to penetrate the flesh 120 and pass through the loop 28a held on the looper arm 29. Continued movement of the handle members together causes the looper arm 29 to retract to the right as viewed in FIG. 13 i.e. causes the needle 24 to move relative to the looper arm 29 to its advanced position in order to clear the needle loop 28a from the looper arm as described above.

Figure 14:
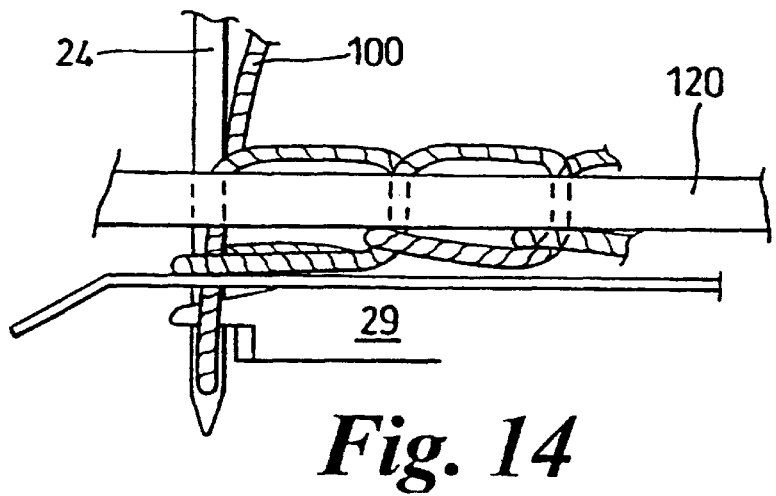

In FIG. 14, the handle members 91,92 are moving apart and this enables the looper arm 29 to advance in order to pick up new thread from the needle.

When a seam has been completed, the seam may be tied off by finishing with the needle penetrating through the flesh, slacking off the thread on the bobbin, drawing the thread from the needle and holding it whilst the needle is retracted. This leaves ends either side of the flesh which can be tied off. The thread is preferably severed in the thread anchorage tail in order to avoid the need to re-thread the needle.

What is claimed is:

1. A hand held surgical sewing device for suturing tissue comprising an elongate rigid support body having sewing means located at one end of the rigid support body adapted to create a suture in the form of a series of continuous chain stitches, and drive means located at the opposite end of the elongate body for causing operation of the sewing means, the sewing means including a looper arm which forms a longitudinal extension of the elongate support body and a needle arm extending longitudinally adjacent to the looper arm, the needle arm being pivotally mounted at one end to the support body at a position intermediate the opposite ends of the support body so as to be movable about said pivot between a closed position and an open position, the terminal end of the needle arm carrying a sewing needle projecting toward the looper arm, the terminal end of the needle arm being spaced relatively near to the looper arm when the needle arm is at its closed position to enable tissue to be sutured to be trapped therebetween for penetration by said needle and the terminal end of the needle arm being spaced relatively remote from the looper arm when the needle arm is at its open position to space the needle from the tissue and enable the support body to be advanced longitudinally relative to the tissues to be sutured.

2. A sewing device according to claim 1 wherein the drive means is arranged to drive the sewing means through a single sewing cycle only in order to produce a single stitch.

3. A sewing device according to claim 2 wherein the support body comprises an elongate tube.

4. A sewing device according to claim 3 wherein the needle arm is pivotally connected to a push-rod slidably received within said elongate tube and the looper arm being fixedly mounted on one end of the tube.

5. A sewing device according to any of claim 4 wherein stitch length control means are mounted on the end of the tube opposite to said looper arm.

6. A sewing device according to claim 5 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

7. A sewing device according to claim 4 wherein the drive means is manually operable, said rod being connected to the drive means such that on operation of the drive means, the rod is reciprocated between fully retracted and fully extended positions.

8. A sewing device according to any of claim 7 wherein stitch length control means are mounted on the end of the tube opposite to said looper arm.

9. A sewing device according to claim 8 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

10. A sewing device according to claim 7 wherein the drive means comprises a first handle member fixedly mounted on said tube and a second handle member movably connected to the first handle member, the second handle member being connected to said rod.

11. A sewing device according to any of claim 10 wherein stitch length control means are mounted on the end of the tube opposite to said looper arm.

12. A sewing device according to claim 11 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

13. A sewing device according to claim 10 wherein the first and second handle members are biased apart to thereby bias said rod to its fully retracted position.

14. A sewing device according to any of claim 13 wherein stitch length control means are mounted on the end of the tube opposite to said looper arm.

15. A sewing device according to claim 14 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

16. A sewing device according to claim 10 wherein sewing thread is stored on a bobbin mounted on the first handle member, the bobbin being rotatably mounted and tension means being provided to control rotation of said bobbin.

17. A sewing device according to any of claim 16 wherein stitch length control means are mounted on the end of the tube opposite to said looper arm.

18. A sewing device according to claim 17 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

19. A sewing device according to claim 16 wherein the bobbin is arranged to be manually rotated.

20. A swing device according to any of claim 19 wherein stitch length control means are mounted on the end of the tube opposite to said looper arm.

21. A sewing device according to claim 20 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

22. A sewing device according to claim 19 wherein the tension means is manually adjustable.

23. A sewing device according to any of claim 22 wherein stitch length control means are mounted on the end of the tube opposite to said looper arm.

24. A sewing device according to claim 23 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

25. A sewing device according to claim 16 wherein the tension means is manually adjustable.

26. A sewing device according to any of claim 25 wherein stitch length control means are mounted on the end of the tube opposite to said looper arm.

27. A sewing device according to claim 26 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

28. A sewing device according to claim 13 wherein sewing thread is stored on a bobbin mounted on the first handle member, the bobbin being rotatably mounted and tension means being provided to control rotation of said bobbin.

29. A sewing device according to claim 28 wherein the bobbin is arranged to be manually rotated.

30. A sewing device according to any of claim 29 wherein stitch length control means are mounted on the end of the tube opposite to said looper arm.

31. A sewing device according to claim 30 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

32. A sewing device according to claim 29 wherein the tension means is manually adjustable.

33. A sewing device according to any of claim 32 wherein stitch length control means are mounted on the end of the tube opposite to said looper arm.

34. A sewing device according to claim 33 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

35. A sewing device according to claim 28 wherein the tension means is manually adjustable.

36. A sewing device according to any of claim 35 wherein stitch length control means are mounted on the end of the tube opposite to said looper arm.

37. A sewing device according to claim 36 wherein the stitch length control means includes a thread clamp movably mounted on the tube, the thread clamp being adapted to hold a length of thread running from the beginning of a seam sewn by the device and being arranged to be manually moved to thereby advance the needle along the seam being sewn.

38. A sewing device according to any of claim 28 wherein stitch length control means are mounted on the end of the tube opposite to said looper arm.

39. A sewing device according to claim 38 wherein the stitch length control means includes a thread clamp movably mounted on the tube the thread clamp being adapted to hold a length of thread running from the beginning of a seam sewn by the device and being arranged to be manually moved to thereby advance the needle along the seam being sewn.

40. A hand held surgical sewing device for suturing tissue comprising an elongate rigid support body having sewing means located at one end adapted to create a suture in the form of a series of continuous chain stitches, and drive means located at the opposite end of the elongate body for causing operation of the sewing means, the sewing means including a sewing needle mounted on a needle arm which is pivotally mounted on the support body, the needle projecting toward a looper arm, the needle and looper arms forming a longitudinal extension of the elongate support body.

* * * * *

UNITED STATES PATENT AND TRADEMARK OFFICE
CERTIFICATE OF CORRECTION

PATENT NO.    : 6,585,744 B1                                                    Page 1 of 1
DATED         : July 1, 2003
INVENTOR(S)   : John Dalton Griffith It is certified that error appears in the above-identified patent and that said Letters Patent is hereby corrected as shown below:

Column 5,
Line 58, please delete "swing" and insert -- sewing --.

Signed and Sealed this

Twenty-first Day of October, 2003

JAMES E. ROGAN
*Director of the United States Patent and Trademark Office*